US010912901B2

(12) United States Patent
Surendra et al.

(10) Patent No.: US 10,912,901 B2
(45) Date of Patent: Feb. 9, 2021

(54) ACTIVE SMOKE FILTRATION FOR INSUFFLATION

(71) Applicant: Fisher & Paykel Healthcare Limited, Auckland (NZ)

(72) Inventors: Wisnu Arya Surendra, Auckland (NZ); Ali Ghalib Abdul Rahman Ghalib, Auckland (NZ); Shahar Dor-Zidon, Auckland (NZ); Joseph Patrick Walter Strevens, Auckland (NZ); Michael Joseph Blackhurst, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 399 days.

(21) Appl. No.: 15/310,912

(22) PCT Filed: May 15, 2015

(86) PCT No.: PCT/NZ2015/050059
§ 371 (c)(1),
(2) Date: Nov. 14, 2016

(87) PCT Pub. No.: WO2015/174861
PCT Pub. Date: Nov. 19, 2015

(65) Prior Publication Data
US 2017/0080167 A1    Mar. 23, 2017

Related U.S. Application Data

(60) Provisional application No. 61/993,728, filed on May 15, 2014.

(51) Int. Cl.
*A61M 13/00* (2006.01)
*A61B 1/313* (2006.01)
(Continued)

(52) U.S. Cl.
CPC .......... *A61M 13/006* (2014.02); *A61M 13/00* (2013.01); *A61B 1/015* (2013.01);
(Continued)

(58) Field of Classification Search
CPC .. A61M 13/00; A61M 13/006; A61M 13/003; A61M 16/16; A61M 16/109;
(Continued)

(56) References Cited

U.S. PATENT DOCUMENTS 3,680,283 A * 8/1972 Jones, Jr. ............. B01D 53/261
  55/302
4,735,603 A * 4/1988 Goodson ................ A61B 18/20
  600/560

(Continued)

FOREIGN PATENT DOCUMENTS

EP        1295621 A2    3/2003
WO   WO 2011/078701 A1   6/2011
(Continued)

OTHER PUBLICATIONS

International Search Report; PCT/NZ2015/050059; dated Jul. 28, 2015; 6 pages.

*Primary Examiner* — Tiffany Legette
(74) *Attorney, Agent, or Firm* — Knobbe Martens Olson and Bear, LLP

(57) ABSTRACT

An active smoke filtration unit is used to remove smoke during laparoscopic surgery. The active smoke filtration unit is part of a recirculation circuit. The recirculation circuit is pneumatically isolated from a primary flow generator, such as an insufflator, by a valve assembly. The active smoke filtration unit can be housed separately from the valve assembly or together with the valve assembly. The recirculation circuit can include a humidifier to heat and humidify the insufflation gases.

21 Claims, 8 Drawing Sheets

(51) Int. Cl.
    *A61M 16/10*     (2006.01)
    *A61M 16/16*     (2006.01)
    *A61B 1/015*     (2006.01)
    *A61M 39/24*     (2006.01)

(52) U.S. Cl.
    CPC .......... *A61B 1/3132* (2013.01); *A61M 16/107* (2014.02); *A61M 16/109* (2014.02); *A61M 16/1055* (2013.01); *A61M 16/16* (2013.01); *A61M 39/24* (2013.01); *A61M 2205/3344* (2013.01); *A61M 2205/75* (2013.01)

(58) Field of Classification Search
    CPC ............ A61M 16/1095; A61M 16/161; A61M 16/1055; A61M 16/107; A61M 2205/3344; A61M 2205/75; A61M 39/24; A61B 1/015; A61B 18/00; A61B 2218/008; A61B 1/3132
    See application file for complete search history.

(56) References Cited

U.S. PATENT DOCUMENTS

| | | | | |
|---|---|---|---|---|
| 5,098,375 | A * | 3/1992 | Baier | A61M 13/006 600/560 |
| 5,411,474 | A * | 5/1995 | Ott | A61M 13/003 600/560 |
| 6,134,716 | A * | 10/2000 | Richardson | A41D 13/11 2/171.2 |
| 6,544,210 | B1 * | 4/2003 | Trudel | A61B 18/00 604/26 |
| 9,474,512 | B2 * | 10/2016 | Blackhurst | A61B 17/00 |
| 2004/0102731 | A1 * | 5/2004 | Blackhurst | A61B 1/00154 604/26 |
| 2005/0113797 | A1 * | 5/2005 | Ott | A61M 13/003 604/506 |
| 2006/0184096 | A1 * | 8/2006 | Ott | A61M 13/003 604/26 |
| 2007/0088275 | A1 * | 4/2007 | Stearns | A61M 1/28 604/164.01 |
| 2009/0137943 | A1 * | 5/2009 | Stearns | A61B 17/3421 604/26 |
| 2010/0170208 | A1 * | 7/2010 | Matula | A61M 13/003 55/344 |
| 2010/0185139 | A1 * | 7/2010 | Stearns | A61B 17/3474 604/26 |
| 2011/0087160 | A1 * | 4/2011 | Temple | A61M 13/003 604/26 |
| 2012/0165610 | A1 * | 6/2012 | Poll | A61B 1/00119 600/157 |
| 2012/0245509 | A1 * | 9/2012 | Tran | A61B 18/00 604/24 |
| 2012/0330224 | A1 * | 12/2012 | Mailova | A61M 13/003 604/24 |
| 2013/0098360 | A1 * | 4/2013 | Hurmez | A61M 13/003 128/203.12 |
| 2013/0131580 | A1 * | 5/2013 | Blackhurst | A61B 18/00 604/26 |
| 2013/0317463 | A1 * | 11/2013 | Yao | A61M 1/0031 604/319 |
| 2014/0100517 | A1 * | 4/2014 | Tran | A61M 16/109 604/26 |
| 2015/0151074 | A1 * | 6/2015 | Hermez | A61M 16/0875 128/203.27 |
| 2015/0290402 | A1 * | 10/2015 | Phillips | A61M 13/00 604/26 |
| 2015/0367087 | A1 * | 12/2015 | Dor Zidon | B01J 7/00 604/26 |
| 2017/0000959 | A1 * | 1/2017 | Mantell | A61B 17/3474 |
| 2017/0080167 | A1 * | 3/2017 | Surendra | A61M 13/00 |

FOREIGN PATENT DOCUMENTS

| | | | |
|---|---|---|---|
| WO | WO 2012/040221 A2 | 3/2012 | |
| WO | WO-2014112886 A1 * | 7/2014 | .......... A61M 13/003 |

* cited by examiner

ACTIVE SMOKE FILTRATION FOR INSUFFLATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to active smoke filtration units for use during laparoscopic surgery, More particularly, the present disclosure relates to an active smoke filtration unit that is part of a generally closed recirculation circuit within a laparoscopic surgery insufflation system.

Description of the Related Art

In some systems used for laparoscopic surgery, the gases delivered to the patient are conditioned prior to delivery to the patient. In some such systems, the gases are heated and humidified prior to delivery to the patient, For example, a humidification system can be placed between an insufflator and a surgical cannula, As gases travel towards the patient, the gases are humidified, and heated and/or insulated tubing ensures humidity is not lost before the gases reach the patient.

During laparoscopic surgery, smoke and other debris can be produced as a result of the cautery process, for example but without limitation. The smoke can form within the body cavity and can cloud the vision provided to the surgeon through an endoscopic camera that is positioned to view inside the body cavity.

SUMMARY

It is desirable to remove such smoke to improve the vision of the surgeon, It is possible to vent the body cavity and thereby remove smoke. However, maintaining the pressure within the body cavity also is desired. It is also desirable to recirculate and thus reuse insufflation gases, such as carbon dioxide, which reduces overall consumption of such gases and allows for the use of smaller gas containers.

By recirculating and filtering the conditioned insufflation gases used during laparoscopic surgery, the debris and smoke from the cautery process can be removed. While filtration apparatus and techniques have been used in the past, those apparatus and techniques have proven to be inefficient, noisy, and less effective than desired.

Accordingly, an improved active filtration system and unit has been developed. The system is considered active because an apparatus such as a compressor, for example but without limitation, is used to create a recirculating flow of insufflation gases through the body cavity. Recirculation of insufflation gases reduces the likelihood of pressure loss during the filtration process. In addition, recirculation of insufflation gases can be viewed as an improvement over a passive system that simply vents the insufflation gases out of the body cavity of the patient to the atmosphere.

By recirculating the insufflation gases in a recirculation circuit that is disposed both inside and outside of the body of the patient, a larger filter can be used than would otherwise be possible to use within the body. Also, when the circuit includes a humidifier, moisture can be maintained within the system, thereby reducing the volume of water used to adequately humidify the gases. A humidifier can heat and humidify the insufflation gases, which can help to reduce disruption to the cellular layer of the peritoneum, thereby mitigating desiccation and subsequent complications such as adhesions, tumor metastasis, and other temperature-related complications.

Recirculating insufflation gases outside of the body of the patient, however, can pose certain challenges, especially when the insufflation gases are conditioned. For example, recirculating gases outside of the body can result in cooling of the gases, which is counter to the goal of heating and humidifying the gases. Entrainment of room air into the recirculation circuit can also result in cooling and drying of the insufflation gases. Moreover, cooling of heated and humidified gases can result in condensation, and condensation can inhibit effective recirculation and/or cloud the vision of the surgeon inside the body cavity.

According to some aspects of the present disclosure, a system for use during laparoscopic surgery comprises a recirculation circuit having an inlet and an outlet. The inlet is configured to connect to a body cavity and the outlet is configured to connect to a gases conduit between a primary flow generator and a connection to the body cavity. The system also comprises a pneumatic isolation feature configured to be positioned between the recirculation circuit and the primary flow generator. The pneumatic isolation feature is in fluid communication with the recirculation circuit. The system further comprises an active filtration unit that is positioned along the recirculation circuit. The active filtration unit comprises a flow generator portion and a filtration portion. The flow generator portion comprises an inlet and an outlet and is configured to create a pressure differential between the inlet and the outlet. The filtration portion comprises a filter adapted to remove smoke and other debris from a gases flow through the recirculation circuit. The system also comprises a condensate management system positioned along the recirculation circuit.

The pneumatic isolation feature can comprise a set of valves. The set of valves can comprise a one-way valve and an overpressure valve. The pneumatic isolation feature can comprise a pressure dampener.

A humidifier can be positioned along a flow path between the primary flow generator and the connection to the body cavity. The humidifier can be positioned along the flow path between the pneumatic isolation feature and the connection to the body cavity. The humidifier can be positioned along the flow path between the outlet of the recirculation circuit and the body cavity such that gases coming from the recirculation circuit pass through the humidifier before returning to the body cavity. The pneumatic isolation feature can be positioned along the flow path between the humidifier and the connection to the body cavity. The recirculation circuit can be positioned in the flow path between the humidifier and the connection to the body cavity. The recirculation circuit can be positioned in the flow path between the pneumatic isolation feature and the connection to the body cavity. The recirculation circuit can be positioned in the flow path to recirculate insufflation gases without entrainment of room air into the insufflation system.

The filter can be disposed between an inlet to the active filtration unit and the flow generator portion. The condensate management system can be positioned upstream of the filter. The condensate management system can comprise a water trap. The water trap can be reusable. The condensate management system can comprise a condenser. The condensate management system can comprise a film or foamed breathable polymer. The film or foamed breathable polymer can comprise a conduit. The condensate management system can comprise a canister. The canister can contain a substance with an affinity to water. The substance can comprise a foam material. The substance can comprise a chemical that absorbs water. The condensate management system can comprise a desiccant that is located with the filtration portion. The condensate management system can comprise a heated conduit. The condensate management system can comprise a tube containing an absorbent material. The absorbent material can comprise a sponge or foam.

The flow generator portion can comprise a pump. The pump can comprise a diaphragm compressor. The pump can comprise a radial compressor. The pump can comprise a peristaltic pump. The pump can comprise two interconnected rotors.

According to some aspects of the present disclosure, an active filtration unit configured for use during laparoscopic surgery comprises a filtration portion and a flow generator portion that are positioned in a flow path defined within a housing. The housing comprises an inlet, an outlet, at least a part of the filtration portion, and at least a part of the flow generator portion. The flow path is defined between the inlet and the outlet.

The flow path can be at least partially heated.

A system can comprise a primary flow generator and a recirculation circuit comprising the active filtration unit. The system can comprise a humidifier fluidly coupled to the primary flow generator by a supply conduit and fluidly coupled to the recirculation circuit by at least one tube. The system can comprise a condensate management system. The condensate management system can be at least partially defined within the housing of the active filtration unit. The primary flow generator can comprise an insufflator. A valve assembly can be positioned between the primary flow generator and the recirculation circuit. The valve assembly can comprise a check valve. The valve assembly can comprise an overpressure valve.

According to some aspects of the present disclosure, a recirculating filtration unit configured for use during laparoscopic surgery comprises a filtration portion, a flow generator portion, and a valve assembly that are positioned in a flow path defined within a housing. The housing comprises an inlet, an outlet, the valve assembly, at least a part of the filtration portion, and at least a part of the flow generator portion. The flow path is defined between the inlet and the outlet.

The flow path can be at least partially heated. The valve assembly can comprise a check valve. The valve assembly can comprise an overpressure valve.

A system can comprise a primary flow generator and a recirculation circuit comprising the recirculating filtration unit. The system can comprise a humidifier fluidly coupled to the primary flow generator by a supply conduit and fluidly coupled to the recirculation circuit by at least one tube. The system can comprise a condensate management system. The condensate management system can be at least partially defined within the housing of the recirculating filtration unit. The primary flow generator can comprise an insufflator.

Certain features, aspects and advantages of the apparatus and systems disclosed herein can be used with heated and humidified or otherwise conditioned insufflation systems, with non-conditioned insufflation systems, and with other systems used for laparoscopic surgery applications.

BRIEF DESCRIPTION OF THE DRAWINGS

Specific embodiments and modifications thereof will now be described with reference to the following figures.

DETAILED DESCRIPTION

Figure 1:
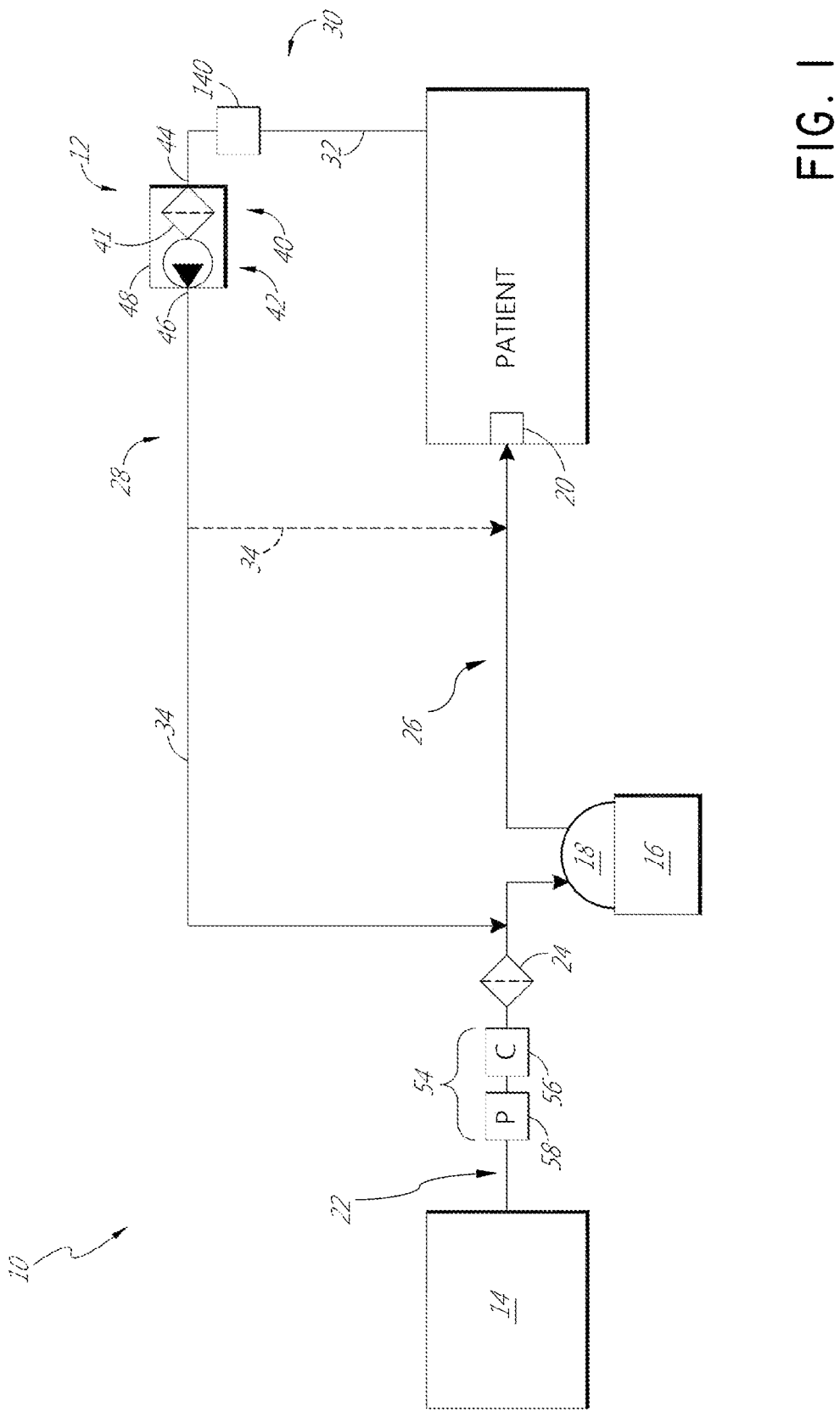
FIG. 1 is a schematic illustration of a first insufflation system.

With reference now to FIG. 1, an example insufflation system 10 that comprises an active filtration unit 12 is illustrated schematically. In some configurations, the active filtration unit 12 is specifically configured to be disposable (i.e., a consumable product). In other configurations, the active filtration unit 12 can be integrated into other components and/or be sterilizable.

The illustrated insufflation system 10 comprises a primary flow generator 14. The primary flow generator 14 can be designed and configured to control at least one of the pressure and the flow rate of gases that will be supplied to the patient during use. The primary flow generator 14 can have any suitable configuration. In some configurations, the primary flow generator 14 can comprise a compressed gases cylinder and a regulator valve assembly. In some configurations, the primary flow generator 14 can comprise a pump that supplies insufflation gases. The primary flow generator 14 can provide a flow rate of less than 45 L/min of insufflation gases. Such configurations are particularly suited for laparoscopic procedures. The primary flow generator 14 can comprise an insufflator. The insufflator 14 can comprise an alma system to warn of gases overpressure events or pressure spikes during a laparoscopic procedure. The insufflation gases can comprise carbon dioxide, for example but without limitation. The insufflator can be provided separate of and connected to the other components of the system (for example, the active filtration unit 12).

To reduce the likelihood of cold, thy gases supplied by the primary flow generator 14 damaging the peritoneum or other body tissues during a surgical procedure, the illustrated insufflation system 10 comprises a humidifier 16. The humidifier 16 can have any suitable configuration. In some configurations, the humidifier 16 features a chamber 18 that contains a liquid (for example, water) and a heating element (for example, a heater plate) that is associated with the chamber 18. In some such configurations, the humidifier 16 can be a humidifier supplied by Fisher & Paykel Healthcare Ltd. known as the MR860 humidifier. In some configurations, the humidifier 16 provides humidification to the system and takes the form of an absorbent material that releases humidity, water vapor or the like into the gases flow. The humidifier 16 can heat and/or humidify the cold, dry gases supplied by the primary flow generator 14. By heating and/or humidifying the cold, dry gases, the peritoneum of a patient can better remain warm and moist during an operation, which can reduce disruption to the cellular layer of the peritoneum by mitigating desiccation and subsequent complications such as adhesions, tumor metastasis, and other temperature-related complications.

In some configurations, the humidifier 16 can be positioned between the primary flow generator 14 and a delivery component 20 through which heated and/or humidified gases can be introduced to the patient. In some configurations, the delivery component 20 can comprise a cannula, such as a Veress needle, which is a spring-loaded needle used to create pneumoperitoneum for laparoscopic surgery. In other configurations, the delivery component 20 can comprise any suitable apparatus through which heated and/or humidified gases can be introduced to the patient.

The primary flow generator 14 can be connected to an inlet of the humidifier 16 with a supply conduit 22. The supply conduit 22 can be any conduit suitable to transport cold, dry gases from the primary flow generator 14. The supply conduit 22 can be a single section of tubing or can be multiple sections of tubing connected together to define a gases delivery channel from the primary flow generator 14 to the humidifier 16.

A filter 24 can be positioned along the supply conduit 22 at a location between the primary flow generator 14 and the humidifier 16. In some configurations, the filter 24 can be a mechanical filter. In some configurations, the filter 24 can be a high-efficiency bacterial filter. In some configurations, the filter 24 is a pleated mechanical HEPA filter. In some configurations, the efficiency of the filter 24 can be BFE 99.9999%, VFE 99.9999% with a filtration ability of 0.3 micron. In some configurations, the filter 24 is hydrophobic. In some configurations, the filter 24 can incorporate a 15 mm connection and a 22 mm connection. In some configurations, a barb adaptor also can be included with the filter 24. In other configurations, the filter 24 can comprise any suitable apparatus to filter the gases transported by the supply conduit 22.

An outlet of the humidifier 16 can be connected to the delivery component 20 using an insufflation conduit 26. The insufflation conduit 26 can be thermally insulated and/or can be heated. In some configurations, the insufflation conduit 26 can incorporate a heater element that wraps around a wall of the insufflation conduit 26. The heater element can be positioned outside of the wall, outside of the lumen, inside of the wall or inside of the lumen of the insufflation conduit 26. By using a heated and/or insulated insufflation conduit 26, the temperature and/or humidity of the conditioned gases can be better maintained during transit from the humidifier 16 to the delivery component 20. The insufflation conduit 26 can be a single section of tubing or can be multiple sections of tubing connected together to define a gases delivery channel from the humidifier 16 to the delivery component 20 keeping in mind a desire to supply the conditioned gases at or above the dew point temperature.

In some configurations, the insufflation conduit 26 can be connected to the delivery component 20 using a connector. In some such configurations, the connector can comprise a rotating luer lock. In some such configurations, the rotating luer lock can be a standard luer fitting compatible with ISO 594-1:1986 and ISO 594-2:1998.

Figure 2:
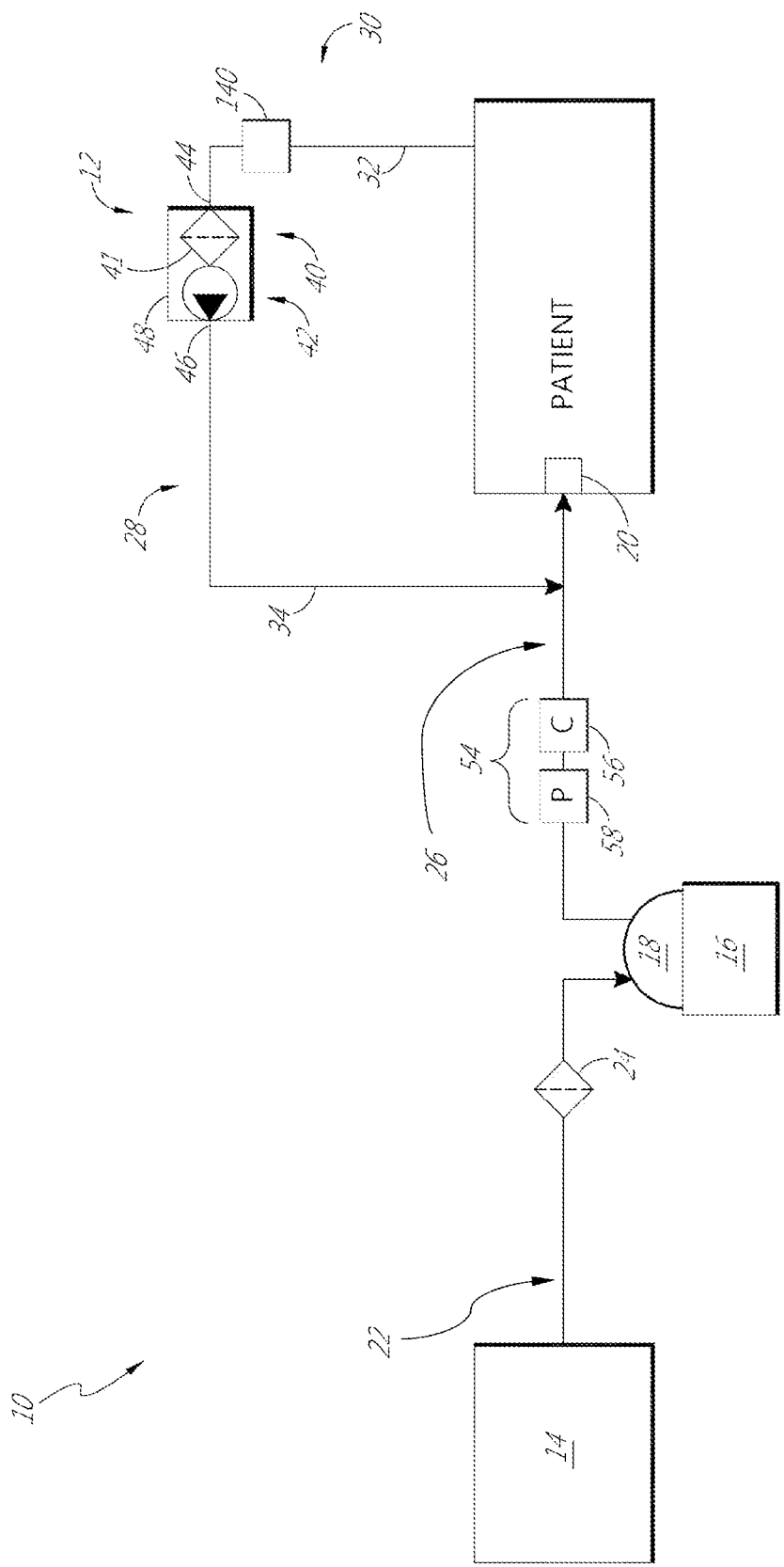
FIG. 2 is a schematic illustration of a second insufflation system.

As illustrated in FIGS. 1 and 2, the active filtration unit 12 can be disposed along a recirculation circuit 28. In some configurations, such as that shown in FIG. 1, the recirculation circuit 28 can extend between the patient and the supply conduit 22. In the configuration of FIG. 1, the recirculation circuit 28 connects to the supply conduit 22 at a location between the filter 24 and the humidifier 16. As such, the illustrated recirculation circuit 28 does not include the bacterial filter 24. As illustrated, the humidifier 16 can be positioned within the recirculation circuit 28 (see FIG. 1). In some configurations, the humidifier 16 is positioned not within the recirculation circuit (see FIG. 2). Accordingly, as shown in FIG. 2, the recirculation circuit 28 can extend between the patient and the insufflation conduit 26, which bypasses both the bacterial filter 24 and the humidifier 16. When the humidifier 16 is positioned within the recirculation circuit 28, humidity can be added to the recirculating gases before the gases are reintroduced to the body cavity. When the humidifier 16 is positioned not within the recirculation circuit 28 (see FIG. 1), then the gases being reintroduced to the body may have less humidity, which can improve the optical clarity.

In some configurations, the recirculation circuit 28 comprises a tube 30 that is configured to interconnect the patient with the supply conduit 22 or the insufflation conduit 26. The tube 30 can comprise one or more sections of tubing. In some configurations, a first section 32 of the tube 30 interconnects the active filtration unit 12 with the patient and a second section 34 of the tube 30 interconnects the active filtration unit 12 with the supply conduit 22 (FIG. 1) or the insufflation conduit 26 (FIG. 2).

In some configurations, the tube 30 is insulated. In some configurations, the tube 30 comprises a heating element. The heating element can be positioned outside of the wall of the tube 30, inside of the wall of the tube 30, outside of the lumen of the tube 30 and/or inside of the lumen of the tube 30. As the gases being withdrawn from the body cavity have a high humidity content, the heating element can reduce or eliminate the likelihood of condensation of the water vapour as the gases are transported through the tube 30. in some configurations, the heating element of the tube 30 is in electrical communication with the heating element of the insufflation conduit 26. In some configurations, the heating element of the tube 30 is controlled by a controller that also controls the heating element of the insufflation conduit 26. In some configurations, the controller controls the heating element of the tube 30 separately of the heating element of the insufflation conduit 26. In some configurations, the controller controls the heating element of the tube 30 together with the heating element of the insufflation conduit 26. In some configurations, the controller forms a portion of the humidifier 16. In some configurations, the controller forms a portion of the primary flow generator 14. In some configurations, the controller forms a portion of the active filtration unit 12. In some configurations, the controller is separate from the primary flow generator 14, the humidifier 16, and the active filtration unit 12.

As discussed above, by insulating and/or heating portions of the tube 30 (e.g., one or both of the first section 32 and the second section 34), the conditioned gases that have been delivered to the patient are less likely to cool in transit to and/or from the active filtration unit 12. Accordingly, in configurations in which one or both of the first section 32 and the second section 34 of the tube 30 are insulated and/or heated, the moisture present within the conditioned gases is less likely to condense during transit through the recirculation circuit 28. The conditioned gases are also less likely to drop in temperature or humidity while flowing through the recirculation circuit 28 because the insufflation gases are recirculated without entrainment of room air. In some configurations, the dew point temperature of the recirculating gases is exceeded throughout the recirculation circuit 28.

Figure 3:
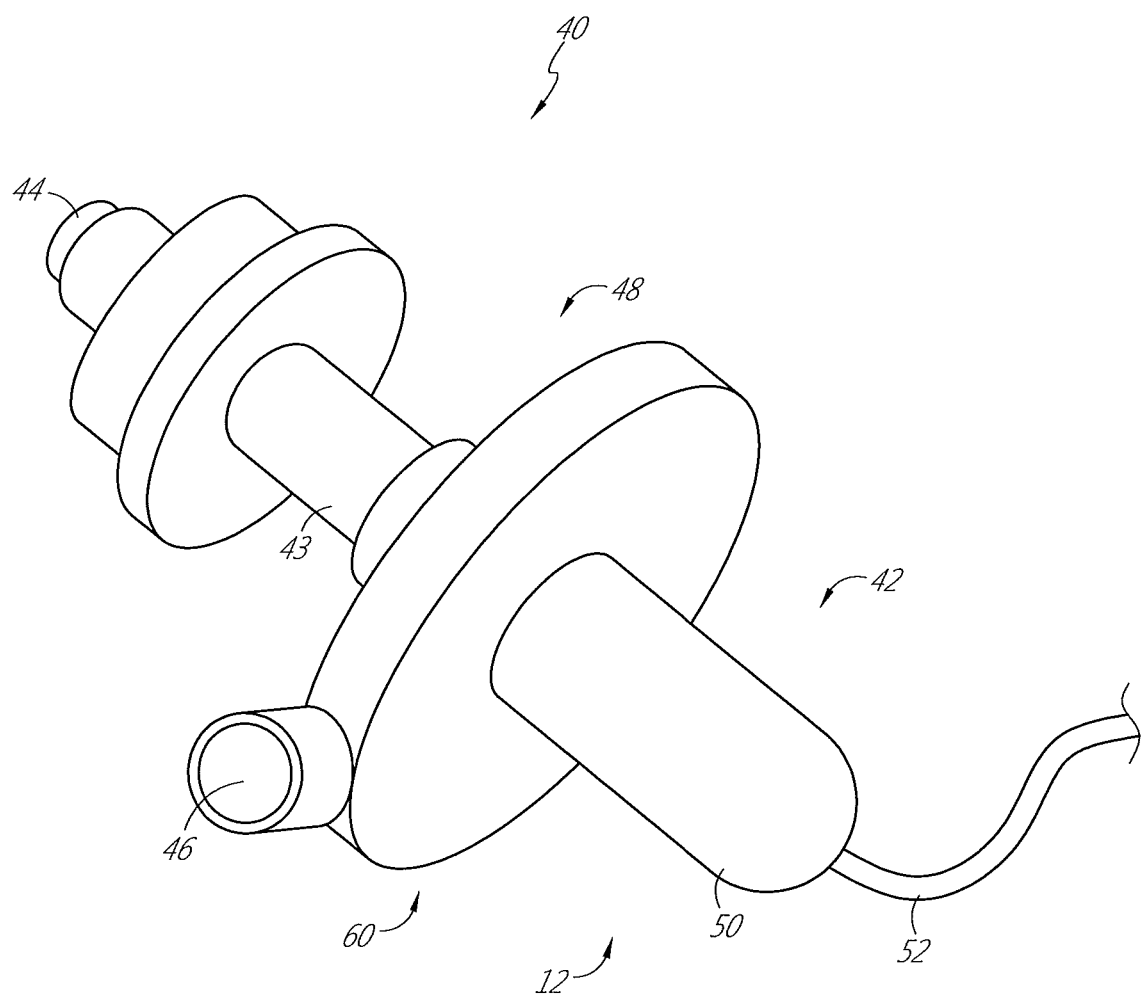
FIG. 3 is an illustration of a smoke filtration unit.

With reference now to FIG. 3, the active filtration unit 12 generally comprises a filtration portion 40 and a flow generator portion 42 that can be connected by a flow connector 43. While the illustrated configuration features an integrated unit having both the filtration portion 40 and the flow generator portion 42, it is possible to separate the filtration portion 40 and the flow generator portion 42 into two separate units. In some configurations, the filtration unit 12 is configured to reduce noise. For example, the flow generator portion 42 can be mechanically isolated from the other components of the active filtration unit 12. In some configurations, the flow generator portion 42, which includes a flow generator, pump, or the like, can be physically or mechanically decoupled from a housing of the active filtration unit. In some configurations, the flow generator portion 42 can be muffled, surrounded, enclosed, enveloped, or isolated using a sound absorbing material. Other configurations also are possible.

The active filtration unit 12 also comprises an inlet 44 and an outlet 46. Gases are drawn in from the patient to the active filtration unit 12 through the inlet 44 and returned toward the patient through the outlet 46. In the illustrated configuration, the filtration portion 40 is positioned between the inlet 44 and the flow generator portion 42. In some configurations, the flow generator portion 42 can be positioned between the inlet 44 and the filtration portion 40.

In some configurations, at least a portion of a flow path through the active filtration unit 12 between the inlet 44 and the outlet 46 can be heated. In some configurations, only the filtration portion 40 is heated. In some configurations, the flow generator portion 42 is heated. In some configurations, a majority of the flow path between the inlet 44 and the outlet 46 can be heated. In some configurations, almost the entire flow path through the active filtration unit 12 can be heated. In some configurations, the entire flow path from the inlet 44 to the outlet 46 can be heated.

The active filtration unit 12 comprises a housing 48. The housing 48 can be configured to be clipped onto a drape or other component within the operating theater. In some configurations, the active filtration unit 12 and/or the tube 30 that is attached to the active filtration unit 12 can be draped over the patient in the operating theater. The housing 48 in the illustrated configuration defines the inlet 44, the outlet 46, and the internal passages between the inlet 44 and the outlet 46. The housing 48 generally encloses the flow generator portion 42. The housing 48 generally encloses the filtration portion 40.

The active filtration unit 12 creates pressure differences that cause gases to flow through the recirculation circuit 28. To create the desired pressure differences, the flow generator portion 42 can be a compressor or the like. Because the active filtration unit 12 works by creating pressure differences, the illustrated active filtration unit 12 may only work with some types of insufflators. In some configurations, the flow generator portion 42 can be configured similarly to the configuration shown and described in U.S. Provisional Patent Application No. 61/738,910, filed on Dec. 18, 2012 and entitled Impeller and Motor Assembly, or U.S. Provisional Patent Application No. 61/507,384, filed Jul. 13, 2011 and entitled Impeller and Motor Assembly, each of which is hereby incorporated by reference in its entirety.

In some configurations, the flow generator can be a pump 60 (for example, a peristaltic pump, a radial compressor, a diaphragm compressor, a rotor system, or the like). In some configurations, the pump 60 can be incorporated into the primary flow generator 14. In some configurations, the pump 60 can be incorporated into the insufflator. In some configurations, the pump 60 is designed to be positioned outside of a sterile zone. As used herein, "sterile zone" means an area within an operating theatre/clinic within which only sterile equipment can be used, and into which only those personnel who have gone through surgical scrubbing and the gowning process can enter. In some configurations, the insufflation system 10 can be configured such that the pump 60 will be positioned within the sterile zone.

In configurations where the active filtration unit 12 has a pump 60 positioned within the sterile zone, the pump 60 (and/or any other portion of the active filtration unit 12 designed to be positioned within the sterile zone) is either disposable (that is, a single use pump) or capable of being repeatedly sterilized (for example, through the use of steam autoclave or dry heat oven) so that it can be re-sterilized between uses. If configured to be a single use pump, the gas flow path would need to be sterile. In some such configurations, the gas flow path can be decoupled from the motor or other operating component that may be in direct contact with the gas flow path.

In some configurations, the flow generator portion 42 can comprise an impeller. A motor 50 can be used to drive the impeller. The flow generator portion 42, and the active filtration unit 12 in general, can be powered from mains or can be battery powered. An electrical cable 52 can be used to provide power and/or control signals and can be connected to the motor 50.

The motor 50 may be any motor suitable for generating high flow rates. In some configurations, the flow generator portion 42 is rated for high flow rates to overcome pressure in the system. In other words, high flow rates are desired to achieve a recirculating flow of gases in the active filtration unit 12 and the recirculation circuit 28. In the illustrated configuration, the motor 50 (in combination with the impeller and related flow paths within the housing 48) creates a pressure differential between the inlet 44 and the outlet 46 to generate a flow of gases that removes smoke from a body cavity of a patient.

Figure 4:
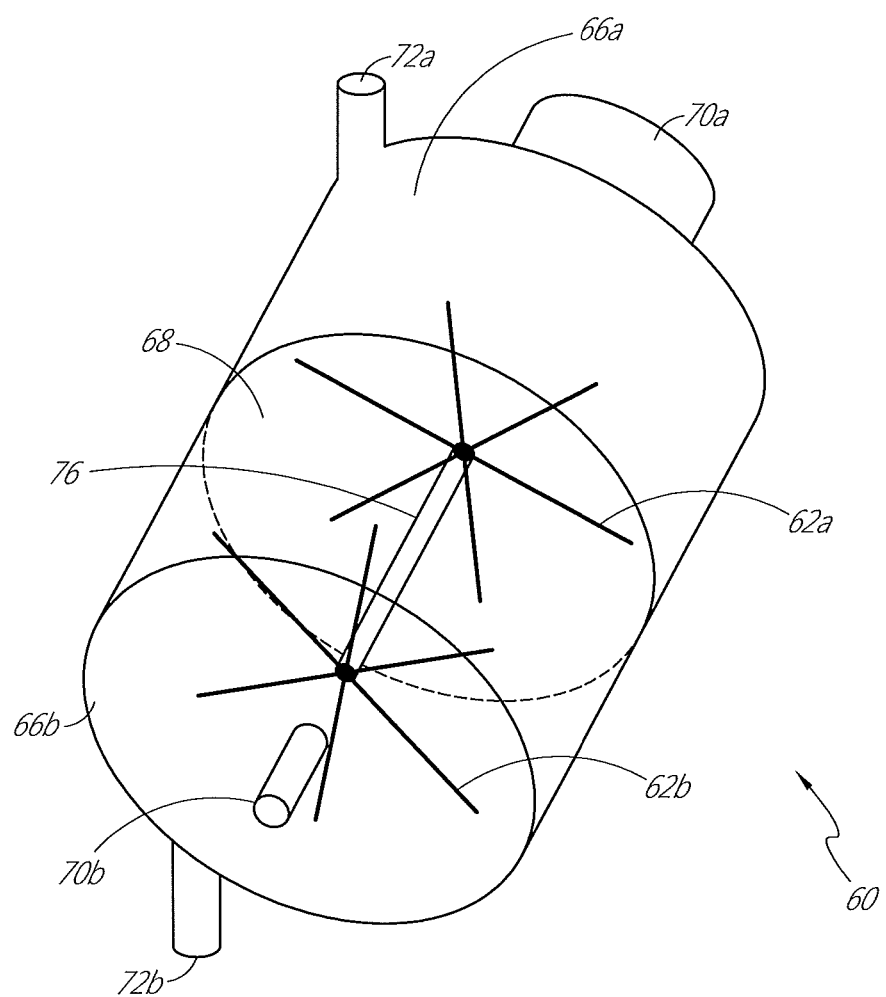
FIG. 4 is a schematic view of a motorless pump having two interconnected rotors.

Use of the motor 50 can increase the cost of the system, particularly when a single use pump 60 is desired. With reference to FIG. 4, a pump is illustrated that includes two rotationally connected rotors 62a, 62b. Chambers 66a, 66b can be separated by a wall or other dividing member 68. The two chambers 66a, 66b preferably are sealed from each other such that gases cannot be exchanged between the two chambers 66a, 66b. Each of the chambers includes an inlet 70a, 70b and an outlet 72a, 72b. The flow of the recirculation circuit 28 passes through the first chamber 66a while a secondary flow from another system passes through the second chamber 66b. For example, the secondary flow can be created by a suction source such as an in-theatre source or a compressed bottle.

In some configurations, the first rotor 62a is positioned in the first chamber 66a while the second rotor 62b is positioned in the second chamber 62b. The two rotors 62a, 62b are connected by a shaft 76. In some configurations, a gear train, a magnetic coupling or the like also can be used to connect the two rotors 62a, 62b keeping in mind a desire for one of the rotors 62b to drive the other of the rotors 62a. For example, the magnetic coupling can allow rotational coupling without a direct physical coupling, which simplifies isolating the gases in the first chamber 66a from the gases in the second chamber 66b.

The secondary flow will drive the second rotor 62b. Because the second rotor 62b and the first rotor 62a are joined for rotational movement, the first rotor 62a will be driven by the second rotor 62b. Rotation of the first rotor 62a causes flow within the recirculation circuit 28. Accordingly, in the illustrated configuration, no motor is required, which allows for a less expensive pump and one that can be designed to be a single use pump. In some configurations, only the components that come into contact with the flow of the recirculation circuit 28 are designed to be single use, whilst the remaining components of the pump can be reused.

Figure 5:
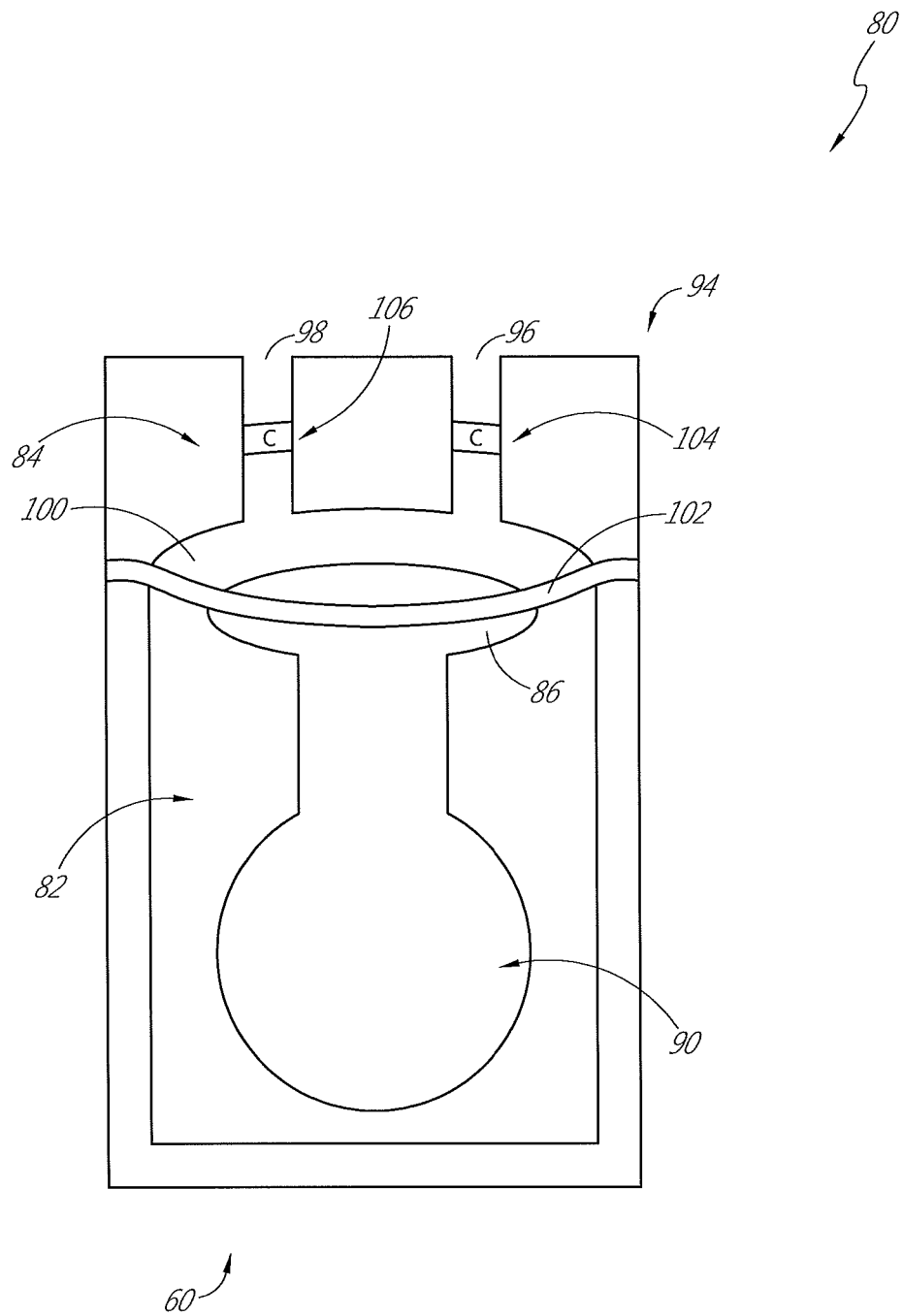
FIG. 5 is a schematic view of a diaphragm pump.

With reference now to FIG. 5, a diaphragm compressor 80 is illustrated. The diaphragm compressor 80 can be used as the pump 60. In some configurations, at least a portion of the diaphragm compressor 80 can be configured for single use. For example, the diaphragm compressor 80 comprises a drive portion 82 and a flow generator portion 84. The drive portion 82 can include a piston 86 that is connected to the flow generator portion 84. The piston 86 can be moved in any suitable manner. In the illustrated configuration, a the piston 86 is connected to a motor 90. The motor 90 can be a rotary motor. The motor 90 can be an electric motor. The piston 86 and the motor 90 are not in communication with the gases of the recirculation circuit 28. Rather, only the flow generator portion 84 is in fluid communication with the gases of the recirculation circuit 28. Accordingly, the piston 86 and the motor 90 can be reused.

The flow generator portion 84 can be configured to be one-time or single use. In some configurations, the flow generator portion 84 can be configured as a disposable cartridge 94 or the like. The flow generator portion 84 can include an inlet 96 and an outlet 98. The inlet 96 and the outlet 98 can be connected to a chamber 100 that includes a diaphragm 102. Check valves 104, 106 or one-way valves can be included along the flow path through the flow generator portion 84 to help direct flow through the flow generator portion 84 of the diaphragm compressor 80. Movement of the diaphragm 102 acts to pull gases into the chamber 100 and then expel the gases from the chamber 100. While the diaphragm compressor 80 does incorporate the motor 90, and thus has a higher initial cost than the dual rotor design discussed above, the use of a disposable cartridge 94 that includes the chamber 100, the inlet 96, the outlet 98 and the diaphragm 102 allows for a simple and cost effective single use design.

Figure 6:
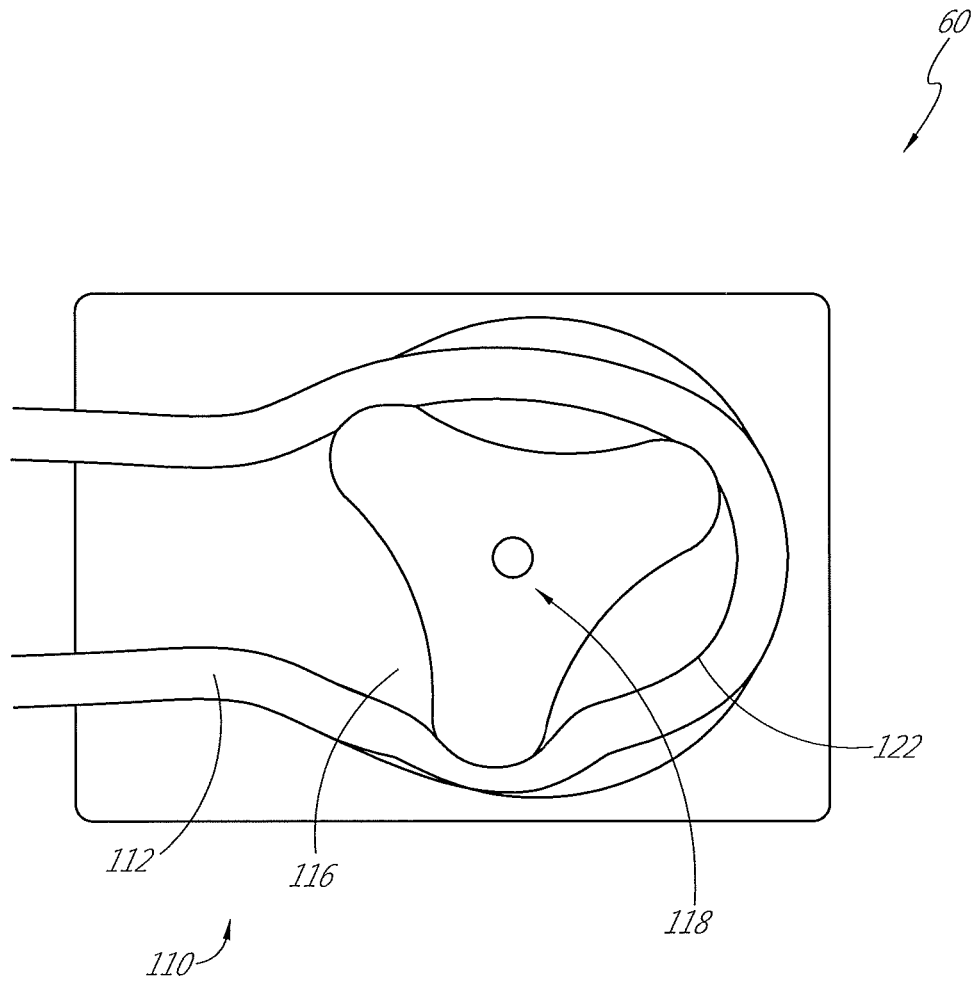
FIG. 6 is a schematic view of a peristaltic pump.

With reference to FIG. 6, a peristaltic pump 110 is illustrated that can be used as the pump 60 of the active filtration unit 12. The pump 110 includes a disposable length of tubing 112. As illustrated, the tubing 112 can be positioned within a chamber 116. The chamber 116 can include a rotary member 118. The rotary member 118 and a wall 122 within the chamber 116 contact and squeeze the tubing 112. The rotary member 118 can be driven in any suitable manner. In some configurations, a motor drives the rotary member 118. In some configurations, a rotary motor drives the rotary member 118. In some configurations, an electric motor drives the rotary member 118.

In the peristaltic pump 110, the gases of the recirculation circuit 28 are constrained to contact only the tubing 112. As such, the peristaltic pump 110 generally can be reused while the tubing 112 is discarded. In some configurations, the chamber 116, the rotary member 118, and the tubing 112 can be supplied as a cartridge. Thus, the cartridge can be easily connected and disconnected, which facilitates simplified reuse. In some configurations, only the tubing 112 is discarded and reused. Any other suitable configuration also can be used that isolates the portion of the pump 110 that must be discarded while preserving the majority of the pump 110 for reuse.

Figure 8:
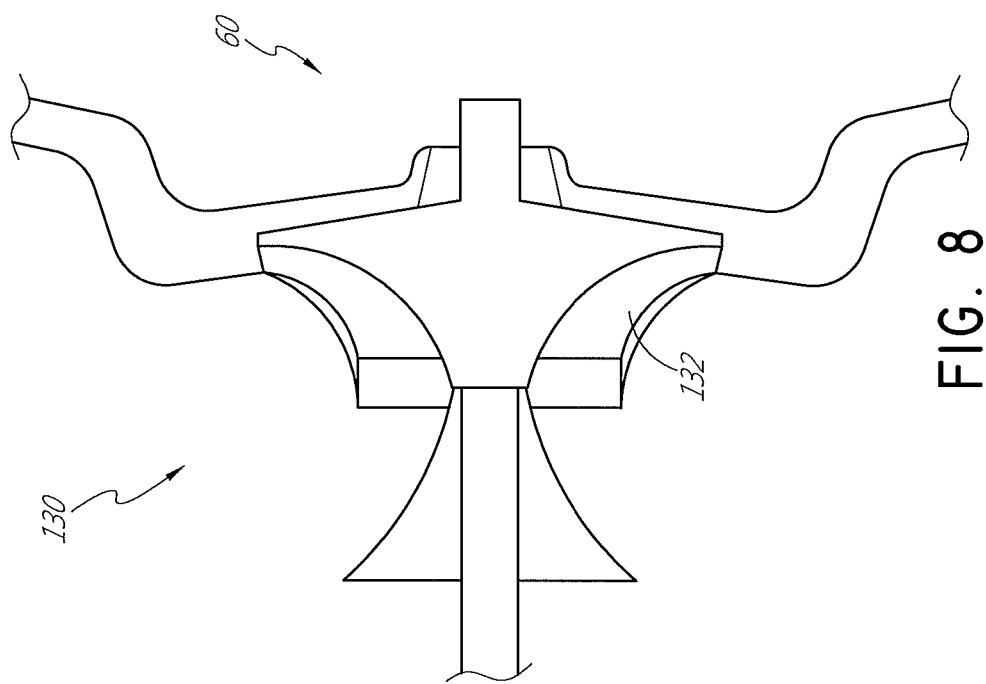
FIG. 7 and FIG. 8 are schematic views of a radial compressor.
Figure 7:
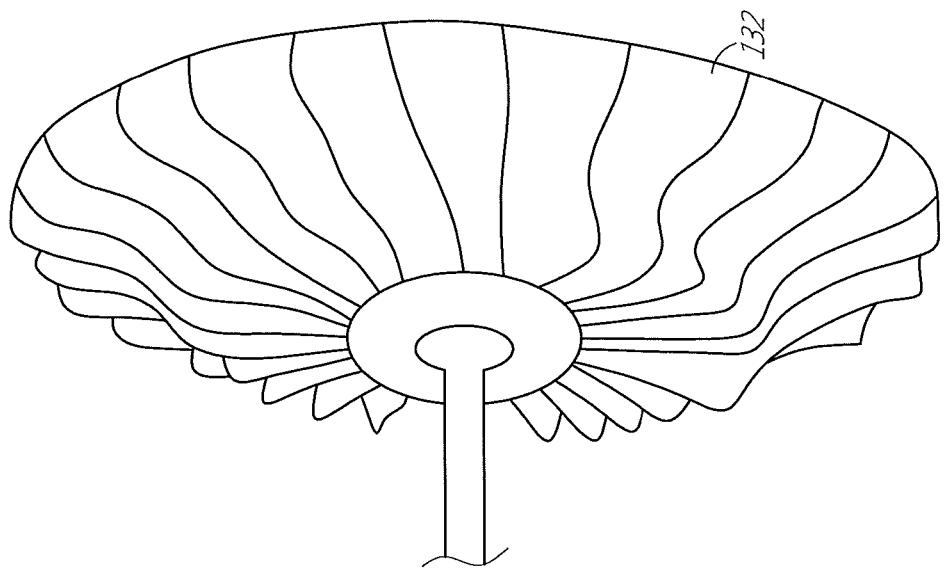

As discussed above, any suitable type of pump 60 can be used. For example, as shown in FIG. 7 and FIG. 8, the pump 60 can be a radial compressor 130 or the like. The radial compressor 130, however, has a vaned member 132 that is in direct contact with the fluid passing through the pump 60. As such, sterilizing the radial compressor 130 might be more difficult or labor intensive and, due to the use of a motor and other mechanical components, disposing of the entire radial compressor 130 might be cost prohibitive.

With reference again to FIGS. 1 and 2, the filtration portion 40 can comprise a mechanical filter 41. The filtration portion 40, and specifically the filter 41 within the filtration portion 40, is provided to filter dirty gases after they emerge from the body cavity. In some configurations, the filter 41 can be positioned in a cannula that vents to the atmosphere or at an inlet or an outlet of the flow generator portion 42, In some configurations, the filter 41 can be, for example, but not limited to, HEPA, chemical, electrostatic, or the like, keeping in mind a desire to filter out smoke particles and other debris. In some configurations, the filter 41 can comprise a carbon filter that is paired with the filter 41. The carbon filter, or another suitable filter, can be used to remove odors, if desired.

The mechanical filter 41 can be contained within the housing 48. Accordingly, in some instances, the humidity encountered within the active filtration unit 12 can shorten the life span of the mechanical filter 41 if sufficient condensation is allowed to occur. In some configurations, at least a portion of the active filtration unit 12 can be heated while at least a portion of the tube 30 or another portion of the active filtration unit 12 can comprise a hydrophilic material, such as a sulfonated tetrafluoroethylene-perfluoro copolymer (e.g., Nafion®, a registered mark of E. I. du Pont de Nemours and Company) or a poly(ether-ester) block copolymer (for example, Sympatex®, a registered mark of Sympatex Technologies GmbH), for example but without limitation ("breathable materials" as used herein). In some such configurations, the breathable materials can be formed in a film state or in a foamed state. Such configurations, however, can allow moisture to be lost to the ambient atmosphere through the tube 30. In such configurations, the moisture lost can be replaced using the humidifier 16 when the primary flow generator 14 is operating, or by including the humidifier 16 within the recirculation circuit 28 (for example, as shown in FIG. 1). Accordingly, lowered humidity levels may be experienced by the filter 41 while maintaining a desired degree of humidification in the body cavity.

Gases leaving the body cavity generally contain a high level of humidity. The humidity can result in condensation upon an unheated filter 41 or unheated tubing 30. The active filtration unit 12 and/or the recirculation circuit 28 can include a condensate management unit 140. While it is possible to omit a condensate management unit 140, use of the condensate management unit 140 can increase the operating time of the system 10. By positioning the condensate management unit 140 upstream of the filter 41 and/or filtration portion 40, the condensate management unit 140 can help reduce the likelihood of the condensate causing clogging of the filter 41. Preferably, the condensate management unit 140, as illustrated, is positioned along the portion of the recirculation circuit 28 that extends from the body cavity (i.e., the. inlet into the recirculation system) to the filtration portion 40. In some configurations, the condensate management unit 140 can be positioned at, near or adjacent an inlet to the filter 41 or filtration portion 40. In some configurations, the filter 41 can be positioned at, near or adjacent an outlet of the condensate management unit 140. The condensate management unit 140 can have any suitable configuration.

In some configurations, a water trap or other form of condenser can be used. The water trap or condenser can use a less-heated, unheated or cooled material that causes vapour to condense into the water trap or condenser. In some configurations, the material can comprise a metal mesh. The material can form a wall or a portion of a wall of the tube 30. The material can extend into the lumen of the tube 30.

Any other suitable material and/or configuration also can be used. In some configurations, the flow from the body cavity toward the filtration portion 40 passes through the material of the water trap. The water trap can comprise a removable and/or reusable chamber. In such configurations, the water trap chamber can be removed, emptied, cleaned and reinstalled. In some such configurations, the water trap chamber can be autoclaved or sterilized between subsequent uses. In some configurations, the water trap does not have a removable chamber; instead, the water trap itself can be removed, emptied, cleaned and reinstalled. In some such configurations, the water trap can be autoclaved or sterilized between subsequent uses.

In some configurations, a desiccant or an absorbent material can be used to capture condensate. For example but without limitation, the desiccant or absorbent material can be a chemical or foam that has an affinity to water or that is a hygroscopic substance. In some configurations, the desiccant or absorbent material can be silica gel. In some configurations, the desiccant or absorbent material can be a foam or sponge. The desiccant or absorbent material can be used with a water trap or can be used in configurations not having a water trap. In some configurations, the desiccant or absorbent material can be contained within a canister. In some configurations, the desiccant or absorbent material can be positioned internally along at least a portion of the tube 30 located between the inlet into the tube 30 (that is, the inlet end positioned at or within the body cavity) and the filtration portion 40. In some configurations, the desiccant or absorbent material can be positioned within or near the housing 48 of the filtration portion 40. In some configurations, the desiccant or absorbent material can be positioned within the housing 48 but upstream of the filter 41.

Any suitable mechanism can be provided to pneumatically isolate the recirculation circuit 28 from the primary flow generator 14 (e.g., the insufflator). With reference again to FIGS. 1 and 2, a valve assembly 54 can be used to control and regulate the pressures within the insufflation system 10. The valve assembly 54 can pneumatically isolate the recirculation circuit 28 from the primary flow generator 14. The valve assembly 54 can be positioned in various locations suitable for isolating the active filtration unit 12 and the recirculation circuit 28 from the primary flow generator 14. In the illustrated configuration, the valve assembly 54 can comprise a one-way valve 56 (e.g., a check valve) and an overpressure valve 58 (e.g., a pressure relief valve). In other configurations, the valve assembly 54 can comprise any suitable set of valves.

The one-way valve 56 can be used to reduce or eliminate the likelihood of pressure generated by the active filtration unit 12 being sensed at the primary flow generator 14 by being transmitted through the insufflation conduit 26. In some configurations, the one-way valve 56 can be positioned between the humidifier 16 and the recirculation circuit 28. In some configurations, the one-way valve 56 can be positioned between the primary flow generator 14 and the humidifier 16. For example, by positioning the one-way valve 56 between the primary flow generator 14 and the humidifier 16, the compressible volume between the primary flow generator 14 and the one-way valve 56 can be reduced, which can improve control.

When the active filtration unit 12 is operating, the one-way valve 56 is closed, which effectively reduces or eliminates the likelihood of the primary flow generator 14 sensing the pressure inside the peritoneum. In many cases, the primary flow generator 14 has an alarm or the like that will sound when a pressure is sensed that exceeds a predetermined pressure or when the pressure spikes. However, when the one-way valve 56 closes, the quick movement of the one-way valve 56 can cause a phenomenon known as fluid hammer. Fluid hammer can cause the primary flow generator 14 to mistakenly sense an overpressure condition, which can result in an alarm even though the pressure inside of the body has not changed in any significant manner. Accordingly, in some configurations, the one-way valve 56 can be paired with the overpressure valve 58, which can function as a hammer arrestor. The overpressure valve 58 may open if the pressure within the upstream flow path exceeds a desired level. Thus, the one-way valve 56 can isolate the active filtration unit 12 from the primary flow generator 14 while the overpressure valve 58 can protect against undesirable pressures upstream of the one-way valve 56. In some configurations, the one-way valve 56 and the overpressure valve 58 can be integrated into a single unit that limits backflow toward the primary flow generator 14 while also venting excess pressure when the pressure exceeds a predetermined threshold.

In some configurations, a valve can be provided that allows the primary flow generator 14 to vent to the ambient atmosphere and to separate the primary flow generator 14 from the recirculation circuit 28 that includes the active filtration unit 12. In some configurations, a continuously open fixed throttle valve can be used to dampen pressure spikes instead of the overpressure valve 58.

Figure 9:
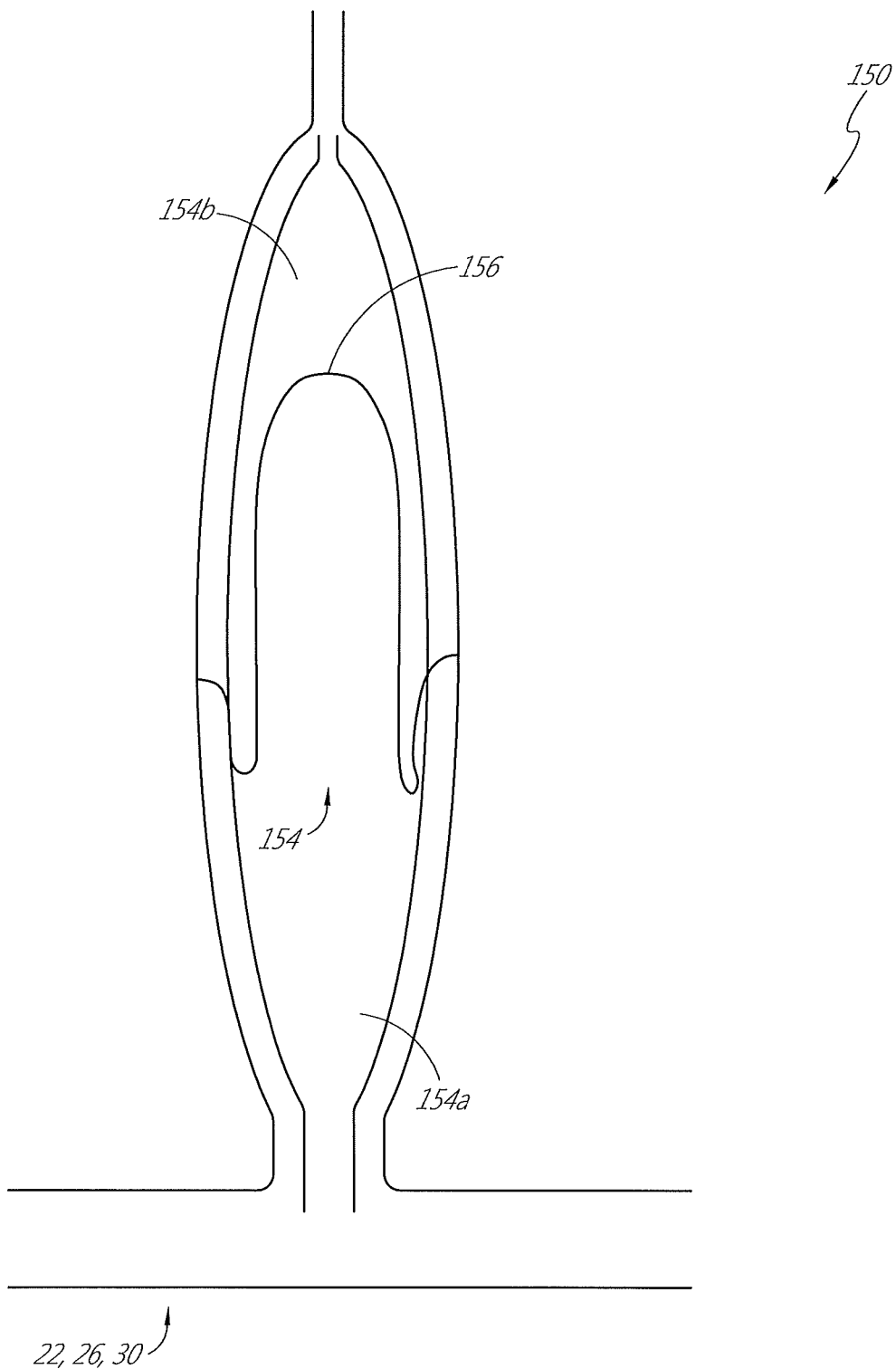
FIG. 9 is a schematic view of a pressure dampener.

In some configurations, a pressure dampener 150, such as that shown in FIG. 9 can be used instead of, or in addition to, the valve assembly 54. The pressure dampener 150 can be positioned along the supply conduit 22 or the insufflation conduit 26. The pressure dampener 150 can isolate the primary flow generator 14 from the recirculation circuit 28, which reduces or eliminates the likelihood of the primary flow generator 14 alarming as a result of operation of the active filtration unit 12. In effect, the pressure dampener 150 releases or absorbs excess pressure. For example, during a pressure spike, the pressure dampener 150 absorbs the pressure spike, which reduces the likelihood of operation of the active filtration unit 12 causing the primary flow generator 14 to alarm. The pressure dampener 150 has an added benefit of not temporarily blinding the primary flow generator 14 from the recirculation circuit 28. Thus, the pressure dampener 150 enables the primary flow generator 14 to continue monitoring or checking a pressure within the body cavity during use of the active filtration unit 12 and the recirculation circuit 28.

As illustrated in FIG. 9, the pressure dampener 150 can comprise a chamber 154. The chamber 154 can be divided into a first subchamber 154a and a second subchamber 154b by a bladder 156 or any other suitable dividing structure. The first subchamber 154a can be in direct fluid communication with the supply conduit 22, the insufflation conduit 26, or the tube 30. In some configurations, the first subchamber 154a is directly connected to the supply conduit 22. The second subchamber 154b can be pressurized using any suitable fluid. For example, in some configurations, the second subchamber 154b can be pressurized using compressed air or gas. When a pressure pulse is created within the insufflation system 10, fluid enters the first subchamber 154a, displacing the bladder 156, compressing the gas within the second subchamber 154b and absorbing the shock of the pressure pulse. When the pressure pulse subsides, the gas within the second subchamber 154b expands and pushes the fluid (e.g., carbon dioxide) back into the connected conduit 22, 26, 30, thereby virtually eliminating pressure variation and pulsation.

The active filtration unit 12 can be operated in any suitable manner. In some configurations, the active filtration unit 12 can be activated and deactivated manually as desired by the surgeon or other operator. An algorithmic control can be implemented using a suitable controller or the like. The controller can be associated with any component of the insufflation system (for example, the active filtration unit 12, the primary flow generator 14, the humidifier 16) or the controller can be a separate component from the rest of the components of the insufflation system (for example, have a housing and be separate of and separable from all of the other components that may incorporate controllers or the like, such as the active filtration unit 12, the primary flow generator 14, and the humidifier 16). In some such configurations, the controller can be integrated into the insufflator or gases source and the active filtration unit 12 can be controlled from the insufflator or gases source.

In some configurations, an algorithmic control may comprise a timer. In some configurations, because the smoke contained within the body cavity can be filtered through the system within about 20-30 seconds, the active filtration unit 12 is cycled into an active state for 20-30 second increments. In some configurations, an algorithm that comprises a timer may control how long the active filtration unit 12 is turned off and/or how long the active filtration unit 12 is turned on. In some configurations, the active filtration unit 12 can be attached to a cautery device and triggered by current through the cautery device. In some configurations, the active filtration unit 12 can be designed for constant or semi-constant use during a surgical procedure.

The active filtration unit 12 acts to remove smoke and debris while enabling the reuse of the conditioned insufflation gases. The moisture and insufflation gases taken from the patient are retained and, therefore, recirculated back to the patient. Desirably, a generally consistent pressure is maintained within the body cavity during operation of the active filtration unit 12. In other words, the pressure within the body cavity preferably does not significantly decrease during the procedure (i.e., decrease to a level that causes operation of the insufflator to add pressure). In instances in which the pressure within the body cavity decreases during the procedure, the insufflator or other flow generator can provide additional insufflation gases, which can return the pressure to a desired level within the body cavity.

Unless the context clearly requires otherwise, throughout this specification, the words "comprise", "comprising", and the like, are to be construed in an inclusive sense as opposed to an exclusive or exhaustive sense, that is to say, in the sense of "including, but not limited to".

Although the disclosed apparatus and systems have been described by way of example and with reference to possible embodiments thereof, it is to be understood that modifications or improvements may be made thereto without departing from the scope of the disclosure. The disclosed apparatus and systems may also be said broadly to comprise the parts, elements, and features referred to or indicated in this specification, individually or collectively, in any or all combinations of two or more of said parts, elements, or features. Furthermore, where reference has been made to specific components or integers having known equivalents, then such equivalents are herein incorporated as if individually set forth.

Any discussion of the prior art throughout this specification should in no way be considered as an admission that such prior art is widely known or forms part of common general knowledge in the field.

What is claimed is:

1. A system for use during laparoscopic surgery, the system comprising:
    a recirculation circuit configured to connect to a body cavity of a patient to receive gases passing from the body cavity of the patient and reintroduce said gases to the body cavity of the patient;
    a primary flow generator configured to control the pressure of said gases supplied to the patient, wherein the primary flow generator comprises an insufflator;
    a pneumatic isolation feature between the recirculation circuit and the primary flow generator that pneumatically isolates the recirculation circuit from the primary flow generator, the pneumatic isolation feature in fluid communication with the recirculation circuit;
    an active filtration unit positioned along the recirculation circuit, the active filtration unit comprising a flow generator portion and a filtration portion, the flow generator portion comprising an inlet and an outlet, the flow generator portion configured to create a pressure differential between the inlet and the outlet, the filtration portion comprising a filter adapted to remove smoke and other debris from said gases flowing through the recirculation circuit;
    a condensate management system positioned along the recirculation circuit; and
    a humidifier for humidifying said gases being delivered to the body cavity of the patient, wherein the humidifier is in fluid communication with the recirculation circuit and configured to add humidity to said gases flowing through the recirculation circuit before said gases are reintroduced to the body cavity of the patient.

2. The system of claim 1, wherein the pneumatic isolation feature comprises a pressure dampener.

3. The system of claim 1, wherein the recirculation circuit is positioned in the flow path between the pneumatic isolation feature and a connection to the body cavity of the patient.

4. The system of claim 1, wherein the filter is disposed between an inlet to the active filtration unit and the flow generator portion.

5. The system of claim 1, wherein the condensate management system is positioned upstream of the filter.

6. The system of claim 1, wherein the condensate management system comprises a condenser.

7. The system of claim 1, wherein the condensate management system comprises a desiccant that is located with the filtration portion.

8. The system of claim 1, wherein the condensate management system comprises a heated conduit.

9. The system of claim 1, wherein the condensate management system comprises a film or foamed breathable polymer.

10. The system of claim 9, wherein the film or foamed breathable polymer comprises a conduit.

11. The system of claim 1, wherein the condensate management system comprises a tube containing an absorbent material.

12. The system of claim 11, wherein the absorbent material comprises a sponge or foam.

13. The system of claim 1, wherein the recirculation circuit comprises a tube configured to connect the body cavity of the patient to a gases conduit between the primary flow generator and a connection to the body cavity of the patient, the tube configured to receive gases from the body cavity of the patient and recirculate the gases to the body cavity of the patient through the gases conduit.

14. The system of claim 13, wherein the tube comprises a first section configured to connect the active filtration unit and the body cavity of the patient, and a second section connecting the active filtration unit and the gases conduit.

15. The system of claim 1, wherein the pneumatic isolation feature comprises a set of valves.

16. The system of claim 15, wherein the set of valves comprises a one-way valve.

17. The system of claim 15, wherein the set of valves comprises an overpressure valve.

18. The system of claim 1, wherein the humidifier is positioned along a flow path between the primary flow generator and a connection to the body cavity of the patient.

19. The system of claim 18, wherein the humidifier is positioned along the flow path between the pneumatic isolation feature and the connection to the body cavity of the patient.

20. The system of claim 18, wherein the humidifier is positioned along the flow path between an outlet of the recirculation circuit and the connection to the body cavity of the patient such that gases passing through the recirculation circuit pass through the humidifier.

21. The system of claim 18, wherein the recirculation circuit is positioned in the flow path between the humidifier and the connection to the body cavity of the patient.

* * * * *